United States Patent [19]

Macor

[11] Patent Number: 5,688,809

[45] Date of Patent: Nov. 18, 1997

[54] 5-HETEROARYLINDOLE DERIVATIVES

[75] Inventor: John E. Macor, Penfield, N.Y.

[73] Assignee: Pfizer Inc., New York, N.Y.

[21] Appl. No.: 687,555

[22] PCT Filed: Dec. 8, 1994

[86] PCT No.: PCT/IB94/00407

§ 371 Date: Oct. 7, 1996

§ 102(e) Date: Oct. 7, 1996

[87] PCT Pub. No.: WO95/21836

PCT Pub. Date: Aug. 17, 1995

Related U.S. Application Data

[63] Continuation of Ser. No. 194,553, Feb. 10, 1994, abandoned.

[51] Int. Cl.$^6$ ............... C07D 403/04; C07D 471/04; A61K 31/415; A61K 31/44

[52] U.S. Cl. ............... 514/303; 514/222.5; 514/223.8; 514/241; 514/242; 514/252; 514/255; 514/259; 514/266; 514/269; 514/307; 514/311; 514/338; 514/361; 514/362; 514/363; 514/364; 514/365; 514/367; 514/372; 514/374; 514/375; 514/378; 514/381; 514/383; 544/2; 544/180; 544/238; 544/242

[58] Field of Search ............... 548/305.1; 546/118; 544/264; 514/394, 266, 303

[56] References Cited

FOREIGN PATENT DOCUMENTS 93123396  5/1992  WIPO.

*Primary Examiner*—Johann Richter
*Assistant Examiner*—Laura L. Stockton
*Attorney, Agent, or Firm*—Peter C. Richardson; Paul H. Ginsburg; B. Timothy Creagan

[57] ABSTRACT

The present invention relates to compounds of the formula

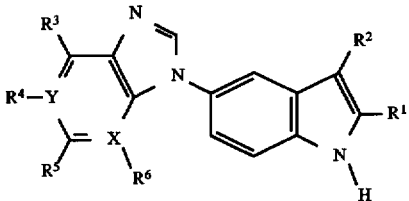

The present invention also relates to intermediates for the preparation of compounds of the formula I, pharmaceutical compositions and method of use.

11 Claims, No Drawings

5-HETEROARYLINDOLE DERIVATIVES

This application is a 371 of PCT/IB94/00407 filed Dec. 8, 1994 which is a continuation of Ser. No. 08/194,553 filed Feb. 10, 1994, now abandoned.

BACKGROUND OF THE INVENTION

The present invention relates to indole derivatives, intermediates for their preparation, pharmaceutical compositions containing them, and their medicinal use. The active compounds of the present invention are potent agonists and antagonists at the benzodiazepine receptor. Agonists and antagonists of the benzodiazepine receptor are useful in the treatment, prevention and diagnosis of anxiety, memory loss, sleep disorders or seizures. The compounds of the invention are also useful in the treatment of an overdose of benzodiazepine drugs.

The use of benzodiazepine receptor ligands in the treatment of anxiety and other disorders has been discussed in "New Trends in Benzodiazepine Research", 24 *Drugs of Today*, 649–663 (1988).

European Patent Publication 499,527, which was published on Aug. 19, 1992, refers to β-carboline derivatives which possess an affinity for benzodiazepine receptors and as such are useful agents in the treatment of degenerative central nervous system disorders, such as Alzheimer's disease.

U.S. Pat. No. 5,243,049, which issued on Sep. 7, 1993, refers to pyrroloquinoline derivatives which are γ-amino butyric acid (GABA) receptor antagonists. These pyrroloquinoline derivatives are claimed to be useful for the treatment of anxiety, sleep disorders, seizures and for enhancing memory.

U.S. Pat. No. 5,066,654, which issued on Nov. 19, 1991, refers to 2-aryl-3-heterocyclicmethyl-3H-imidazo[4,5-B] pyridines that are stated to be useful as anxiolytics and anticonvulsants.

A series of planar azadiindoles, benzannelated pyridoindoles, and indolopyridoimidazoles have been described as molecular probes that are useful for the definition of the molecular recognition elements of the benzodiazepine receptor in *J. Med. Chem.*, 35, 4105–4117 (1992).

International Patent Application WO 93/23396; published Nov. 25, 1993, refers to fused imidazole and triazole derivatives as 5-HT$_1$ receptor agonists that are useful for the treatment of migraine and other disorders.

SUMMARY OF THE INVENTION

The present invention relates to compounds of the formula

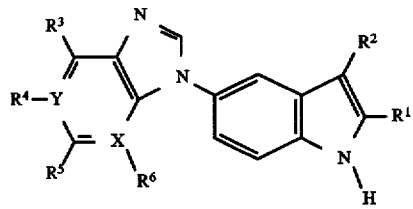

I wherein X and Y are independently carbon or nitrogen;

$R^1$ and $R^2$ are independently selected from hydrogen, $(C_1-C_6)$alkyl, aryl, —$(C_1-C_3)$alkylaryl, —$(CH_2)_n$—$(C_4-C_7)$cycloalkyl, —$(CH_2)_n$CHO, —$(CH_2)_n CO_2 R^7$, —$(CH_2)_n CONR^7 R^8$, 3-succinamido, unsaturated heterocycle, benzo-fused heterocycle, —$(C_1-C_3)$alkyl-unsaturated heterocycle, and —$(C_1-C_3)$alkyl-benzo-fused heterocycle; wherein said unsaturated heterocycle and unsaturated heterocycle moiety of said —$(C_1-C_3)$alkyl-unsaturated heterocycle are selected, independently, from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, 1,2,5-thiadiazinyl, 1,2,5-oxathiazinyl, and 1,2,6-oxathiazinyl; wherein said benzo-fused heterocycle and the benzo-fused heterocyclic moiety of said —$(C_1-C_3)$alkyl-benzo-fused heterocycle are selected, independently, from benzoxazolyl, benzothiazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl and benzoazinyl; wherein each of said unsaturated heterocycle, benzo-fused heterocycle, —$(C_1-C_3)$alkyl-unsaturated heterocycle and —$(C_1-C_3)$alkyl-benzo-fused heterocycle may optionally be substituted on one or more ring carbon atoms with from zero to three substituents, said substituents being independently selected from bromo, chloro, fluoro, $(C_1-C_5)$alkyl, $(C_1-C_5)$alkoxy, $(C_1-C_5)$alkylthio, $(C_1-C_5)$alkylamino, $(C_1-C_4)$alkylsulfonyl, $(C_1-C_5)$dialkylamino, hydroxy, amino, nitro, cyano, trifluoromethyl,

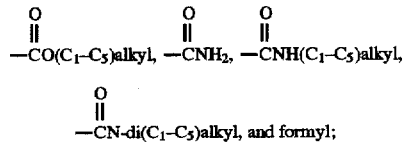

—$CO(C_1-C_5)$alkyl, —$CNH_2$, —$CNH(C_1-C_5)$alkyl,

—$CN$-di$(C_1-C_5)$alkyl, and formyl;

wherein said aryl groups and the aryl moieties of said $(C_1-C_3)$alkylaryl groups are independently selected from phenyl and substituted phenyl, wherein said substituted phenyl may be substituted with from one to three substituents independently selected from $(C_1-C_4)$alkyl, halogen (e.g., fluorine, chlorine bromine or iodine), hydroxy, cyano, carboxamido, nitro, and $(C_1-C_4)$alkoxy;

$R^3$, $R^4$, $R^5$, and $R^6$ are independently selected from hydrogen, $(C_1-C_6)$alkyl, aryl, —$(C_1-C_3)$alkylaryl, —CN, —CHO, $CO_2 R^9$, —$NO_2$, —$CONR^9 R^{10}$, —$(CH_2)_p OH$, —$(CH_2)_p OR^9$, —$(CH_2)_p NR^9 R^{10}$ and halogen (e.g., fluorine, chlorine bromine or iodine); wherein said aryl groups and the aryl moieties of said —$(C_1-C_3)$alkylaryl groups are independently selected from phenyl and substituted phenyl, wherein said substituted phenyl may be substituted with from one to three substituents independently selected from $(C_1-C_4)$alkyl, halogen (e.g., fluorine, chlorine bromine or iodine), hydroxy, cyano, carboxamido, nitro, and $(C_1-C_4)$alkoxy;

$R^7$, $R^8$, $R^9$, and $R^{10}$ are independently selected from hydrogen, $(C_1-C_6)$alkyl, aryl, —$(C_1-C_3)$alkylaryl, unsaturated heterocycle, benzo-fused heterocycle, —$(C_1-C_3)$alkyl-unsaturated heterocycle, and —$(C_1-C_3)$alkyl-benzo-fused heterocycle; wherein said unsaturated heterocycle and unsaturated heterocycle moiety of said —$(C_1-C_3)$alkyl-unsaturated heterocycle are selected, independently, from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, 1,2,5-thiadiazinyl, 1,2,5-oxathiazinyl, and 1,2,6-oxathiazinyl; wherein said benzo-fused heterocycle and the benzo-fused heterocyclic moiety of said —(C₁–C₃)alkyl-benzo-fused heterocycle are selected, independently, from benzoxazolyl, benzothiazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl and benzoxazinyl; wherein each of said unsaturated heterocycle, benzo-fused heterocycle, —(C₁–C₃)alkyl-unsaturated heterocycle and —(C₁–C₃)alkyl-benzo-fused heterocycle may optionally be substituted on one or more ring carbon atoms with from zero to three substituents, said substituents being independently selected from bromo, chloro, fluoro, (C₁–C₅)alkyl, (C₁–C₅)alkoxy, (C₁–C₅)alkylthio, (C₁–C₅)alkylamino, (C₁–C₄)alkylsulfonyl, (C₁–C₅)dialkylamino, hydroxy, amino, nitro, cyano, trifluoromethyl,

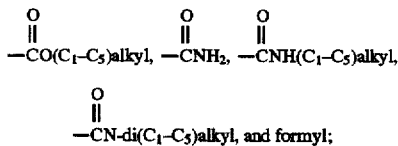

wherein said aryl groups and the aryl moieties of said —(C₁–C₃)alkylaryl groups are independently selected from phenyl and substituted phenyl, wherein said substituted phenyl may be substituted with from one to three substituents independently selected from (C₁–C₄)alkyl, halogen (e.g., fluorine, chlorine bromine or iodine), hydroxy, cyano, carboxamido, nitro, and (C₁–C₄)alkoxy;

n is 0, 1, 2, or 3;

p is 0, 1, or 2;

and the pharmaceutically accepted salts thereof.

The present invention also relates to the pharmaceutically acceptable acid and base addition salts of compounds of the formula I. The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature (e.g., where $R^2$ contains a carboxylate) are capable of forming base salts with various pharmacologically acceptable cations. The chemical bases that are used as reagents to prepare the pharmaceutically acceptable base salts of this invention are, those that form non-toxic base salts with the herein described acidic compounds of formula I. These non-toxic base salts include those derived from such pharmacologically acceptable alkali metal or alkaline-earth metal cations as sodium, potassium, calcium and magnesium.

Preferred compounds of the invention are compounds of the formula I wherein X is carbon, Y is carbon and $R^1$ is hydrogen.

Particularly preferred compounds of the invention are compounds of the formula I wherein $R^3$, $R^5$ and $R^6$ are hydrogen. Specific particularly preferred compounds of the invention are the following:

5-cyano-1-(indol-5-yl)benzimidazole;

5-cyano-1-(3-formylindol-5-yl)benzimidazole;

1-(indol-5-yl)-5-methylbenzimidazole;

5-cyano-1-(3-(cyclohexen-1-yl)indol-5-yl)benzimidazole;

1-(3-formylindol-5-yl)-3H-pyrido[4,5-b]imidazole;

1-(3-(cyclohexen-1-yl)indol-5-yl)-5-methylbenzimidazole;

1-(3-cyclohexylindol-5-yl)-5-methylbenzimidazole; and 1-(3-benzoylindol-5-yl)-5-methylbenzimidazole;

and the pharmaceutically acceptable salts of the foregoing compounds.

Other compounds of formula I include the following:

5-ethyl-1-(3-indol-5-yl)benzimidazole;

5-ethyl-1-(3-methylindol-5-yl)benzimidazole;

5-ethyl-1-(3-ethylindol-5-yl)benzimidazole;

1-(3-cyclohexylindol-5-yl)-5-ethylbenzimidazole;

5-methyl-1-(3-methylindol-5-yl)benzimidazole;

1-(3-ethylindol-5-yl)-5-methylbenzimidazole;

1-(3-isopropylindol-5-yl)-5-methylbenzimidazole;

1-(3-cyclopentylylindol-5-yl)-5-methylbenzimidazole;

1-(indol-5-yl)-5-methoxybenzimidazole;

1-(3-methylindol-5-yl)-5-methoxybenzimidazole;

1-(3-ethylindol-5-yl)-5-methoxybenzimidazole;

1-(3-cyclohexylindol-5-yl)-5-methoxybenzimidazole;

5-chloro-1-(indol-5-yl)benzimidazole;

5-chloro-1-(3-methylindol-5-yl)benzimidazole;

5-chloro-1-(3-ethylindol-5-yl)benzimidazole;

5-chloro-1-(3-cyclohexylindol-5-yl)benzimidazole;

5-methyl-1-(3-methylindol-5-yl)pyrido[4,5-b]imidazole;

1-(3-cyclohexylindol-5-yl)-5-methylpyrido[4,5-b]imidazole;

5-carboxamido-1-(indol-5-yl)benzimidazole;

5-carboxamido-1-(3-methylindol-5-yl)benzimidazole;

5-carboxamido-1-(3-ethylindol-5-yl)benzimidazole;

5-carboxamido-1-(3-cyclohexylindol-5-yl)benzimidazole;

5-formyl-1-(indol-5-yl)benzimidazole;

5-formyl-1-(3-methylindol-5-yl)benzimidazole;

5-formyl-1-(3-ethylindol-5-yl)benzimidazole;

5-formyl-1-(3-cyclohexylindol-5-yl)benzimidazole;

1-(indol-5-yl)-5-phenylethylbenzimidazole;

1-(3-methylindol-5-yl)-5-phenylethylbenzimidazole;

1-(3-ethylindol-5-yl)-5-phenylethylbenzimidazole;

1-(3-cyclohexyindol-5-yl)-5-phenylethylbenzimidazole;

1-(indol-5-yl)-5-methoxymethylbenzimidazole;

1-(3-methylindol-5-yl)-5-methoxymethylbenzimidazole;

1-(3-ethylindol-5-yl)-5-methoxymethylbenzimidazole;

1-(3-cyclohexylindol-5-yl)-5-methoxymethylbenzimidazole;

5-dimethylaminomethyl-1-(indol-5-yl)benzimidazole;

5-dimethylaminomethyl-1-(3-methylindol-5-yl)benzimidazole;

5-dimethylaminomethyl-1-(3-ethylindol-5-yl)benzimidazole; and 5-dimethylaminomethyl-1-(3-cyclohexylindol-5-yl)benzimidazole.

This invention also relates to a method for treating or preventing a condition or disorder selected from anxiety, panic attacks, sleep disorders, seizures, memory loss, convulsions, and drug abuse in a mammal, preferably a human, comprising administering to said mammal requiring such treatment or prevention an amount of a compound of formula I, or a pharmaceutically acceptable salt thereof, effective in treating or preventing such condition or disorder.

This invention also relates to a pharmaceutical composition for treating or preventing a disorder or condition selected from anxiety, panic attacks, sleep disorders, seizures, memory loss, convulsions, and drug abuse in a mammal, preferably a human, comprising an amount of a compound of formula I, or a pharmaceutically acceptable salt thereof, effective in treating or preventing such disorder or condition and a pharmaceutically acceptable carrier.

This invention also relates to a method for treating or preventing a condition or disorder arising from an increase or decrease in benzodiazepine receptor neurotransmission in a mammal, preferably a human, comprising administering to said mammal requiring such treatment or prevention an amount of a compound of formula I, or a pharmaceutically acceptable salt thereof, effective in treating or preventing such condition or disorder.

This invention also relates to a pharmaceutical composition for treating or preventing a disorder or condition arising from an increase or decrease in benzodiazepine receptor neurotransmission in a mammal, preferably a human, comprising an amount of a compound of formula I, or a pharmaceutically acceptable salt thereof, effective in treating or preventing such condition or disorder and a pharmaceutically acceptable carrier.

This invention also relates to a method for antagonizing or agonizing the benzodiazepine receptor in a mammal, preferably a human, comprising administering to said mammal a benzodiazepine receptor antagonizing or agonizing amount of a compound of formula I, or a pharmaceutically acceptable salt thereof.

This invention also relates to a pharmaceutical composition for antagonizing or agonizing the benzodiazepine receptor in a mammal, preferably a human, comprising administering to said mammal a benzodiazepine receptor antagonizing or agonizing amount of a compound of formula I, or a pharmaceutically acceptable salt thereof, and a pharmaceutically acceptable carrier.

This invention also relates to a method for treating or preventing a condition or disorder selected from anxiety, panic attacks, sleep disorders, seizures, memory loss, convulsions, and drug abuse in a mammal, preferably a human, comprising administering to said mammal a benzodiazepine receptor antagonizing or agonizing amount of a compound of formula I, or a pharmaceutically acceptable salt thereof.

This invention also relates to a pharmaceutical composition for treating or preventing a disorder or condition selected from anxiety, panic attacks, sleep disorders, seizures, memory loss, convulsions, and drug abuse in a mammal, preferably a human, comprising administering to said mammal a benzodiazepine receptor antagonizing or agonizing amount of a compound of formula I, or a pharmaceutically acceptable salt thereof, and a pharmaceutically acceptable carrier.

This invention also relates to a compound of the formula

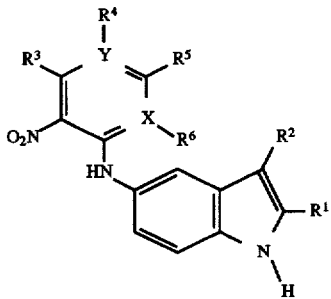

wherein X and Y are independently carbon or nitrogen;

$R^1$ and $R^2$ are independently selected from hydrogen, $(C_1-C_6)$alkyl, aryl, —$(C_1-C_3)$alkylaryl, —$(CH_2)_n$— $(C_4-C_7)$cycloalkyl, —$(CH_2)_n$CHO, —$(CH_2)_n CO_2 R^7$, —$(CH_2)_n CONR^7 R^8$, 3-succinamido, unsaturated heterocycle, benzo-fused heterocycle, —$(C_1-C_3)$alkyl-unsaturated heterocycle, and —$(C_1-C_3)$alkyl-benzo-fused heterocycle; wherein said unsaturated heterocycle and unsaturated heterocycle moiety of said —$(C_1-C_3)$alkyl-unsaturated heterocycle are selected independently from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, 1,2,5-thiadiazinyl, 1,2,5-oxathiazinyl, and 1,2,6-oxathiazinyl; wherein said benzo-fused heterocycle and the benzo-fused heterocyclic moiety of said —$(C_1-C_3)$alkyl-benzo-fused heterocycle are selected independently from benzoxazolyl, benzothiazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl; cinnolinyl and benzoxazinyl; wherein each of said unsaturated heterocycle, benzo-fused heterocycle, —$(C_1-C_3)$alkyl-unsaturated heterocycle and —$(C_1-C_3)$alkyl-benzo-fused heterocycle may optionally be substituted on one or more ring carbon atoms with from zero to three substituents, said substituents being independently selected from bromo, chloro, fluoro, $(C_1-C_5)$alkyl, $(C_1-C_5)$alkoxy, $(C_1-C_5)$alkylthio, $(C_1-C_5)$alkylamino, $(C_1-C_4)$alkylsulfonyl, $(C_1-C_5)$dialkylamino, hydroxy, amino, nitro, cyano, trifluoromethyl,

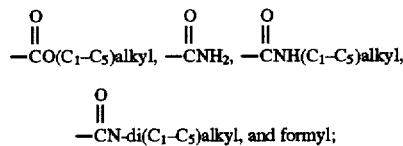

wherein said aryl groups and the aryl moieties of said $(C_1-C_3)$alkylaryl groups are independently selected from phenyl and substituted phenyl, wherein said substituted phenyl may be substituted with from one to three substituents independently selected from $(C_1-C_4)$alkyl, halogen (e.g., fluorine, chlorine bromine or iodine), hydroxy, cyano, carboxamido, nitro, and $(C_1-C_4)$alkoxy;

$R^3$, $R^4$, $R^5$, and $R^6$ are independently selected from hydrogen, $(C_1-C_6)$alkyl, aryl, —$(C_1-C_3)$alkylaryl, —CN, —CHO, $CO_2 R^9$, —$NO_2$, —$CONR^9 R^{10}$, —$(CH_2)_p OH$, —$(CH_2)_p OR^9$, —$(CH_2)_p NR^9 R^{10}$ and halogen (e.g., fluorine, chlorine bromine or iodine); wherein said aryl groups and the aryl moieties of said —$(C_1-C_3)$alkylaryl groups are independently selected from phenyl and substituted phenyl, wherein said substituted phenyl may be substituted with from one to three substituents independently selected from $(C_1-C_4)$alkyl, halogen (e.g., fluorine, chlorine bromine or iodine), hydroxy, cyano, carboxamido, nitro, and $(C_1-C_4)$alkoxy;

$R^7$, $R^8$, $R^9$, and $R^{10}$ are independently selected from hydrogen, $(C_1-C_6)$alkyl, aryl, —$(C_1-C_3)$alkylaryl, unsaturated heterocycle, benzo-fused heterocycle, —$(C_1-C_3)$alkyl-unsaturated heterocycle, and —$(C_1-C_3)$alkyl-benzo-fused heterocycle; wherein said unsaturated heterocycle and unsaturated heterocycle moiety of said —$(C_1-C_3)$alkyl-unsaturated heterocycle are selected independently from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, 1,2,5-thiadiazinyl, 1,2,5-oxathiazinyl, and 1,2,6-oxathiazinyl; wherein said benzo-fused heterocycle and the benzo-fused heterocyclic moiety of said —$(C_1-C_3)$alkyl-benzo-fused heterocycle are selected independently from benzoxazolyl, benzothiazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl and benzoxazinyl; wherein each of said unsaturated heterocycle, benzo-fused heterocycle, —(C$_1$–C$_3$)alkyl-unsaturated heterocycle and —(C$_1$–C$_3$)alkyl-benzo-fused heterocycle may optionally be substituted on one or more ring carbon atoms with from zero to three substituents, said substituents being independently selected from bromo, chloro, fluoro, (C$_1$–C$_5$)alkyl, (C$_1$–C$_5$)alkoxy, (C$_1$–C$_5$) alkylthio, (C$_1$–C$_5$)alkylamino, (C$_1$–C$_4$)alkylsulfonyl, (C$_1$–C$_5$)dialkylamino, hydroxy, amino, nitro, cyano, trifluoromethyl,

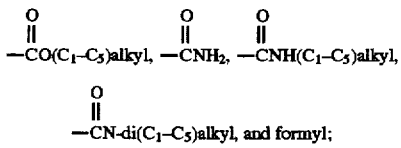

wherein said aryl groups and the aryl moieties of said —(C$_1$–C$_3$)alkylaryl groups are independently selected from phenyl and substituted phenyl, wherein said substituted phenyl may be substituted with from one to three substituents independently selected from (C$_1$–C$_4$)alkyl, halogen (e.g., fluorine, chlorine bromine or iodine), hydroxy, cyano, carboxamido, nitro, and (C$_1$–C$_4$)alkoxy;

n is 0, 1, 2, or 3; and p is 0, 1, or 2.

The compounds of the formula III are useful as intermediates in preparing the compounds of formula I.

Unless otherwise indicated, the alkyl groups referred to herein, as well as the alkyl moieties of other groups referred to herein (e.g. alkoxy), may be linear or branched, and they may also be cyclic (e.g. cyclopropyl, cyclobutyl, cyclopentyl, or cyclohexyl) or be linear or branched and contain cyclic moieties.

DETAILED DESCRIPTION OF THE INVENTION

The compounds of formula I can be prepared according to the methods of scheme 1. In the reaction scheme and discussion that follow, $R^1$, $R^2$, $R^3$, $R^4$, $R^5$, $R^6$, $R^7$, $R^8$, $R^9$, $R^{10}$, X and Y, unless otherwise indicated, are as defined above for formula I.

SCHEME 1

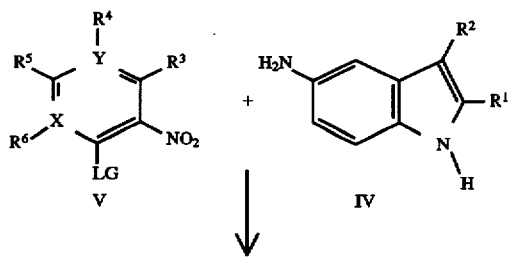

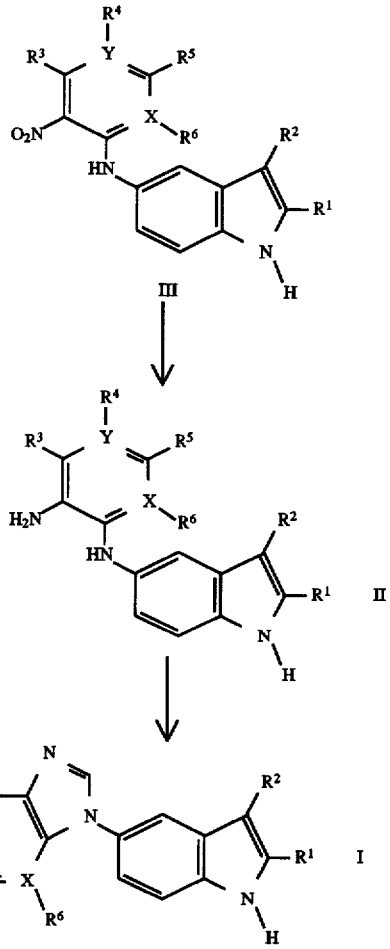

Compounds of formula III can be prepared by reacting a compound of formula IV with a compound of formula V, wherein LG is a leaving group such as, for example, fluoro, chloro, bromo, iodo, methylmercapto (SCH$_3$), methanesulfonyl (SO$_2$CH$_3$), thiophenyl (SPh), or phenylsulfonyl (SO$_2$Ph), under acidic, neutral, or basic conditions in an inert solvent. Basic conditions are preferred. Suitable bases include sodium hydrogen carbonate, sodium carbonate, trialkylamines (including, for example, triethylamine), sodium, and sodium hydride. Triethylamine is the preferred base. Suitable solvents include (C$_1$–C$_4$)alcohols, dioxane, diethyl ether, tetrahydrofuran, acetonitrile, N,N-dimethylformamide, and N-methylpyrrolidine. Ethanol is the preferred solvent. The reaction is usually conducted at a temperature from about 25° C. to about 154° C., preferably about 70° C. to about 80° C.

Compounds of formula II can be prepared from a reduction of compounds of formula III in an inert solvent. This reduction can be mediated either by transition metals or other metal reducing agents. When a transition metal mediates the reduction, a hydrogen source is also used. Suitable transition metals include palladium on carbon, palladium hydroxide on carbon, and platinum oxide. Palladium on carbon is preferred. Suitable hydrogen sources include hydrogen gas, ammonium formate, and formic acid. Hydrogen gas at a pressure of about one to about three atmospheres is the preferred hydrogen source. Three atmospheres of hydrogen gas is the preferred pressure. Suitable solvents include $(C_1-C_4)$alcohols, acetonitrile, N,N-dimethylformamide, and N-methylpyrrolidine. Ethanol is the preferred solvent. Other metal reducing agents include iron sulfate ($FeSO_4$) and zinc (metal)(Zn) in aqueous hydrochloric acid. Of this group, $FeSO_4$ is preferred. When $FeSO_4$ is the reducing agent, suitable solvents include aqueous ammonium hydroxide mixed with ethanol and concentrated aqueous hydrochloric acid. Aqueous ammonium hydroxide (mixed with ethanol) is the preferred solvent. All of the above reduction reactions are usually conducted at a temperature of from about 25° C. to about 100° C., preferably about 25° C. to about 50° C. Compounds of formula II are used directly from the reduction reaction with no purification.

Compounds of formula I are prepared from the reaction of a compound of formula II with a formic acid synthon under neutral or acidic conditions in an inert solvent. Formic acid synthon refers to any molecule that is equivalent to formic acid such that it is capable of reacting with a nuceophile to produce a formyl residue. Suitable formic acid synthons include dimethylformamide dimethylacetal, trimethyl orthoformate, triethyl orthoformate, ethoxymethylenemalononitrile, and diethyl ethoxymethylene malonate. Ethoxymethylenemalononitrile is the preferred formic acid synthon. While neutral conditions are preferred, suitable acid catalysts may accelerate the reaction. Suitable acid catalysts include p-toluenesulfonic acid, hydrochloric acid and acetic acid. Suitable solvents include $(C_1-C_4)$alcohols, dioxane, diethyl ether, tetrahydrofuran, acetonitrile, N,N-dimethylformamide, and N-methylpyrrolidine. 2-Propanol is the preferred solvent. The reaction is usually conducted at a temperature of from about 25° C. to about 154° C., preferably about 75° C. to about 85° C.

Compounds of formula I wherein $R^2$ is hydrogen can be further modified to form additional compounds of formula I wherein $R^2$ is as described for formula I using methods known to those skilled in the art. For example, treatment of a compound of formula I wherein $R^2$ is hydrogen with a base (preferably an alkyl magnesium halide) in an inert solvent (preferably benzene) at a temperature from about 0° C. to about 80° C., forms a basic indole salt. The indole salt, so formed, is capable of reacting with electrophiles (i.e., alkyl halides, Michael acceptors, isocyanides, ketone, aldehydes, acid chlorides, anhydrides) at the C3 position of the indole ring, in an inert solvent (preferably benzene) at a temperature from about 0° C. to about 80° C. leading to compounds of formula I wherein $R^2$ is $(C_1-C_6)$alkyl, —$(C_1-C_3)$ alkylaryl, —$(CH_2)_n$—$(C_4-C_7)$cycloalkyl, —$(CH_2)_n CHO$, —$(CH_2)_n CO_2 R^7$, —$(CH_2)_n CONR^7 R^8$, 3-succinamido, unsaturated heterocycle, benzo-fused heterocycle, —$(C_1-C_3)$alkyl-unsaturated heterocycle, and —$(C_1-C_3)$ alkyl-benzo-fused heterocycle. Alternatively, a compound of formula I wherein either $R^1$ or $R^2$ is hydrogen can be reacted under neutral or acidic conditions with electrophiles leading to compounds of formula I wherein $R^1$ or $R^2$ may independently be $(C_1-C_6)$alkyl, aryl, —$(C_1-C_3)$alkylaryl, —$(CH_2)_n$—$(C_4-C_7)$cycloalkyl, —$(CH_2)_n CHO$, —$(CH_2)_n CO_2 R^7$, —$(CH_2)_n CONR^7 R^8$, 3-succinamido, unsaturated heterocycle, benzo-fused heterocycle, —$(C_1-C_3)$alkyl-unsaturated heterocycle, and —$(C_1-C_3)$ alkyl-benzo-fused heterocycle. The procedures and conditions for carrying out these reactions are known to those skilled in the art, for example, in "Properties and Reactions of Indoles, Isoindoles, and Their Hydrogenated Derivatives," W. A. Reimers, in *The Chemistry of Heterocyclic Compounds* (A. Weissberger and E. C. Taylor, editors), Vol. 25, Part I (W. J. Houlihan, editor), Wiley-Interscience, New York (1972). pp. 70–134, which is hereby incorporated by reference in its entirety.

Compounds of formula IV and formula V are either commercially available or known to those skilled in the art.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The compounds of the formula I which are acidic in nature are capable of forming a wide variety of different salts with various inorganic and organic bases. These salts are all prepared by conventional techniques well known to those of ordinary skill in the art. In general, these salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields of the desired final product.

The compounds of the formula I and the pharmaceutically acceptable salts thereof (hereinafter, also referred to as "the active compounds of the invention") are useful psychotherapeutics and have high affinity for benzodiazepine receptors in the central nervous system. The active compounds of the invention are agonists, partial agonists, antagonists, partial antagonists, or reverse antagonists of the benzodiazepine receptor. The active compounds of the invention which are agonists may be used in the treatment of anxiety, and degenerative central nervous system disorders (e.g. Alzheimer's disease). The active compounds of the invention which are antagonists can be used as anti-convulsants or for the treatment of prevention of seizures or memory loss. The active compounds of the invention which are partial or reverse antagonists may also be useful for memory enhancement.

The affinity of these compounds for benzodiazepine receptors may be measured in an in vitro receptor binding assay such as that described by P. Supavilai and M. Karobath in *Eur. J. Pharm.*, Vol. 70, 183 (1981).

An alternate in vitro receptor binding assay may be used in which guinea pig cerebellum can be the receptor source and [$^3$H]flunitrazepam as the radioligand according to the following process. Either of the above two binding assays may be used to distinguish antagonists, agonists, partial or reverse antagonists and partial agonists. The [$^3$H] flunitrazepam assay is summarized below.

Male Hartley guinea pigs may be decapitated and the cerebellums removed by dissection. Each cerebellum may then be homogenized in 50 mMolar TRIS Acetate buffer (tris[hydroxymethyl]aminomethane acetate). The homogenate may then be centrifuged for 10 minutes at 40,000 g.

The supernatant may then be decanted and the residual pellet diluted with fresh TRIS Acetate buffer. The pellet may then be resuspended and then centrifuged again for 10 minutes at 40,000 g. The supernatant may then be decanted and the pellet washed one more time using the same procedure just described.

After the last wash cycle, the pellet may be resuspended in 50 mM TRIS Acetate buffer. The benzazeipine binding of a compound of formula I can be determined by adding to a tube 750 µl of the tissue suspension prepared according to the above methods with 100 µl of drug or buffer, 150 µl of [3H]-flunitrazepam such that the final concentration of the [3H]-flunitrazepam is 1 nM. The tissue, drug and flunitrazepam may then be incubated for 90 minutes at 0° C. in the dark.

Non-specific binding may be determined by incubating the tissue with flunitrazepam and alprazolam (10 µM) or chlordiazepoxide (10 µM).

After 90 minutes, incubation may be terminated by rapid filtration under vacuum through glassfiber filters (eg., Whatman GF/B®) presoaked in 1% polyethyleneimine (PEI) using a cell harvester. The filter may then be washed three times with ice cold 5 mM TRIS Hydrochloride buffer (pH 7.2). The filters may then be placed in a scintillation vial and soaked in 6 mL of scintillation fluid and allowed to sit overnight.

After standing overnight, the vials may then be vortexed and the radioactivity may be quantified by liquid scintillation counting according to methods well known in the art.

Percent inhibition of specific binding may be calculated for each dose of a compound of formula I. An $IC_{50}$ value may then be calculated from the percent inhibition data. Active compounds of the invention are those which have an $IC_{50}$ of less than 250 nM for the benzodiazepine receptor as measured by either of the above procedures.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use.

Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g. almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form (e.g., in ampules or in multi-dose containers), with an added preservative. The compositions may take such forms as suspensions, solutions or emulsions in oily or aqueous vehicles, and may contain formulating agents such as suspending, stabilizing and/or dispersing agents. Alternatively, the active ingredient may be formulated in powder form for reconstitution with a suitable vehicle, (e.g., sterile pyrogen-free water, before use).

The active compounds of the invention may also be formulated in rectal compositions such as suppositories or retention enemas, (e.g., containing conventional suppository bases such as cocoa butter or other glycerides).

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, (e.g., dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Appropriate dosages of the active compounds of the invention for oral, parenteral, rectal or buccal administration to the average adult human for the treatment of the conditions referred to above will generally range from about 0.1 mg to about 200 mg of the active ingredient per unit dose. Preferably, the unit dosage will range from about 1 mg to about 100 mg. Administration may be repeated, for example, 1 to 4 times per day. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 μg to 10 mg. Administration may be several times daily, for example 2, 3, 4 or 8 times.

The following Examples illustrate the preparation of the compounds of the present invention. Commercial reagents were utilized without further purification. Melting points are uncorrected. NMR data are reported in parts per million (d) and are referenced to the deuterium lock signal from the sample solvent and were obtained on a Bruker 300 MHz instrument. Chromatography refers to column chromatography performed using 32–63 μm silica gel and executed under nitrogen pressure (flash chromatography) conditions. Room temperature refers to 20°–25° C.

EXAMPLE 1

General Synthesis of 1-Indolyl-1H-benz[b] imidazoles and 1-Indolyl-1H-pyrido[4,5-b] imidazoles A mixture of a 5-(2-nitroarylamino)-1H-indole (2.00 mmol) and 10% Palladium (Pd) on carbon (20% by weight) in .absolute ethanol (20 mL) was shaken under a hydrogen atmosphere (3 atm) at room temperature for 8 hours. The resulting reaction mixture was filtered through diatomaceous earth, Celite®, and the filtrate was evaporated under reduced pressure to afford crude 5-(2-aminoarylamino)-1H-indole, which was used directly. Alternatively, a mixture of a 5-(2-nitroarylamino)-1H-indole (2.00 mmol) and iron sulfate ($FeSO_4$) (5.5 g, 20 mmol, 10 equivalents) in ammonium hydroxide/water/ethanol [1:5:3, respectively, 27 mL total volume] was stirred at room temperature for 24 hours. The resulting reaction mixture was then filtered through diatomaceous earth, Celite®. The ethanol was removed from the filtrate by evaporation under reduced pressure. The remaining aqueous mixture was extracted with methylene chloride (3×25 mL), and the organic extracts were combined, dried over magnesium sulfate ($MgSO_4$), and evaporated under reduced pressure to afford crude 5-(2-aminoarylamino)-1H-indole, which was used directly in the next step.

The 5-(2-aminoarylamino)-1H-indole was then combined with either dimethylformamide dimethylacetal (10 mL), triethyl orthoformate/formic acid (5 mL/5 mL), or ethoxymethylene-malononitrile (0.49 g, 4.01 mmol, 2.0 equivalents) in 2-propanol (10 mL) and heated at reflux under nitrogen for 1 to 24 hours, depending on the substrate. When dimethylformamide dimethylacetal was used, the reaction solvent is changed to toluene after 1 hour, a catalytic mount (5 mg) of p-toluenesulfonic acid was added, and the reaction solution was heated at reflux under nitrogen for 12–24 hours depending on the substrate. The resultant reaction solution was then evaporated under reduced pressure, and the residue was triturated or column chromatographed using silica gel (approximately 50 g) and an appropriate solvent system to afford the appropriate 1-indolyl-1H-benz[b]imidazole or 1-indolyl-1H-pyrido[4,5-b]imidazole.

Following this procedure the following compounds were prepared.

A. 5-Cyano-1-(indol-5-yl)benzimidazole 5-(4-Cyano-2-nitrophenylamino)-1H-indole (0.56 g, 2.0 mmoles) was reduced by catalytic hydrogenation, to form 5-(4-cyano-2-aminophenylamino)-1H-indole (0.50 g, 2.0 mmole). The 5-(4-cyano-2-aminophenylamino)-1H-indole was cyclized using ethoxymethylenemalononitrile (0.49 g, 2.0 mmoles) in propanol, and the cyclization reaction was heated for 24 hours. Column chromatography using ethyl acetate/hexanes [1:1] afforded the title compound (94%) as a yellow solid. Mp, 263.0°–264.0° C.; $^{13}C$ NMR (DMSO-$d_6$) δ147.2, 143.5, 137.5, 135.8, 128.5, 128.1, 127.3, 127.0, 125.3, 120.2, 118.2, 116.7, 113.1, 112.6, 104.8, 102.2; HRMS calculated for $C_{16}H_{10}N_4$ 258.0904, found 258.0904. Analytical calculated for $C_{16}H_{10}N_4$: C, 74.40; H, 3.90; N, 21.69. Found: C, 74.20; H, 3.92; N, 21.69.

B. 1-(Indol-5-yl)-5-methylbenzimidazole 5-(4-Methyl-2-nitrophenylamino)-1H-indole (0.47 g, 2.0 mmoles) was reduced by catalytic hydrogenation to form 5-(4-methyl-2-aminophenylamino)-1H-indole (0.41 g, 2.0 mmoles). The 5-(4-methyl-2-aminophenylamino)-1H-indole was cyclized with ethoxymethylenemalononitrile (0.49 g, 2.0 mmole) in propanol, while being heated for 14 hours. Column chromatography using 10% ethyl acetate in methylene chloride afforded the title compound (81%) as a yellow solid. Mp, 215.0°–216.0° C.; $R_f$=0.3 in 10% ethyl acetate in methylene chloride; $^1H$ NMR (DMSO-$d_6$) δ11.43 (br s, NH), 8.42 (s, 1H), 7.76 (d, J=1.4 Hz, 1H), 7.61 (d, J=8.4 Hz, 1H), 7.56 (d, J=0.5 Hz, 1H), 7.52 (t, J=2.6 Hz, 1H), 7.42 (d, J=8.3 Hz, 1H), 7.30 (dd, J=8.5 and 1.7 Hz, 1H), 7.12 (br d, J=8.3 Hz, 1H), 6.56 (dd, J=2.7 and 0.9 Hz, 1H), 2.44 (s, 3H); $^{13}C$ NMR (DMSO-$d_6$) δ156.5, 144.3, 143.8, 137.2, 134.0, 130.0, 129.1, 128.0, 126.4, 119.7, 119.0, 117.3, 113.4, 111.7, 103.0, 21.6; FAB LRMS (m/z, relative intensity) 249 (23), 248 ([MH]$^+$, 100); HRMS calculated for $C_{16}H_{13}N_3$ 247.1107, found 247.1092.

EXAMPLE 2

5-Cyano-1-(3-formylindol-5-yl)benzimidazole

Phosphorus oxychloride (0.54 mL, 5.81 mmol, 1.5 eq) was added to dimethylformamide (10 mL) at room temperature, and to this solution was added 5-cyano-1-(indol-5-yl)benzimidazole (1.00 g, 3.87 mmol). The resulting reaction solution was heated at 40° C. under nitrogen for 2 hours. An aqueous solution of 10% sodium hydroxide (10 mL) was then added, followed by enough solid sodium hydroxide to adjust the pH to above 13. This mixture was heated at reflux under nitrogen for 1 hour, cooled, and the precipitated solid was filtered to afford the title compound (1.00 g, 90%) as an off-white solid. Mp, greater than 200° C.; IR (KBr) 2225, 1675 cm$^{-1}$; $^1H$ NMR (DMSO-$d_6$) δ10.00 (s, 1H), 8.82 (s, 1H), 8.49 (s, 1H), 8.38 (d, J=0.7 Hz, 1H), 8.26 (d, J=2.0 Hz, 1H), 7.78 (d, J=8.6 Hz, 1H), 7.73 (dd, J=8.5 and 1.4 Hz, 1H), 7.67 (d, J=8.4 Hz, 1H), 7.54 (dd, J=8.6 and 2.2 Hz, 1H); LRMS (m/z, relative intensity) 287 (18), 286 (M$^+$, 100), 258 (18), 230 (11). HRMS calculated for $C_{17}H_{10}N_4O$: 286.0853. Found: 286.0870.

EXAMPLE 3

5-Cyano-1-(3-(cyclohexen-1-yl)indol-5-yl) benzimidazole

A solution of sodium methoxide (0.25 g, 4.6 mmol, 3 equivalents), 5-cyano-1-(indol-5-yl)benzimidazole (0.40 g, 1.54 mmol), and cyclohexanone (0.175 mL, 1.69 mmol, 1.1 equivalents) in N,N-dimethylformamide (8 mL) was heated at 130° C. under nitrogen for 12 hours. The solvent was removed by evaporation under reduced pressure, and the residue was partitioned between ethyl acetate (25 mL) and water (25 mL). The organic layer was separated, dried ($MgSO_4$), and evaporated under reduced pressure. Column chromatography of the residue (0.16 g) using silica gel (approximately 5 g) and elution with ethyl acetate/hexanes [1:1] afforded the title compound. (19%) as a pale yellow solid. $R_f$=0.3 in ethyl acetate/hexanes [1:1]; $^1$H NMR (CDCl$_3$) δ10.35 (br s, 1H), 8.18 (s, 1H), 8.05 (s, 1H), 7.80 (s, 1H), 7.45–7.43 (m, 3H), 7.21 (s, 1H), 7.07 (dd, J=8.5 and 1.9 Hz, 1H), 6.04 (br m, 1H), 2.32 (br m, 2H), 2.08 (br m, 2H), 1.72–1.60 (m, 2H), 1.60–1.50 (m, 2H); $^{13}$C NMR (CDCl$_3$) δ145.7, 142.4, 137.5, 136.7, 130.9, 126.8, 125.7, 124.8, 123.8, 123.6, 122.5, 119.5, 119.2, 118.2, 117.2, 112.7, 112.1, 105.6, 28.4, 25.5, 22.9, 22.2.

EXAMPLE 4

1-(3-Formylindol-5-yl)-3H-pyrido[4,5-b]imidazole

A mixture of 5-(3-nitropyrid-2-ylamino)-1H-indole (5.50 g, 21.63 mmol) and 10% palladium on carbon (1.00 g) in absolute ethanol (75 mL) was shaken under a hydrogen atmosphere (3 atm) for 5 hours. The resulting mixture was filtered through Celite®, and the filtrate was evaporated under reduced pressure. The residue (4.95 g) was dissolved in dimethylformamide dimethylacetal (25 mL), and the resulting solution was heated at reflux under nitrogen for 12 hours. The resulting reaction solution was evaporated under reduced pressure, and the residue was suspended in a solution of 10% aqueous sodium hydroxide and ethanol (5:1, respectively, 75 mL). The resulting mixture was heated at reflux under nitrogen for 3 hours. The pH of this mixture was adjusted to pH 7 with concentrated hydrochloric acid (HCl) followed by a saturated solution of sodium hydrogen carbonate. The resulting aqueous mixture was extracted with ethyl acetate (3 times 75 mL). The organic extracts were combined, dried (MgSO$_4$), and evaporated under reduced pressure. The residue was adhered to silica gel (approximately 10 g) using methanol, and this mixture was placed on top of a silica gel plug (200 g). A solution of 5% methanol in ethyl acetate 5 Liters (L) was passed through this silica gel filter. The last 3 L of solvent was evaporated under reduced pressure. Trituration of the residue in hot ethyl acetate afforded the title compound (1.54 g, 29%) as an off-white powder. Mp, >280° C.; $R_f$=0.2 in ethyl acetate; $^1$H NMR (DMSO-d$_6$) δ12.45 (br s, NH), 9.99 is, 1H), 8.86 is, 1H), 8.51 (d, J=1.8 Hz, 1H), 8.45 (s, 1H), 8.43 (dd, J=4.7 and 1.6 Hz, 1H), 8.22 (dd, J=8.0 and 1.5 Hz, 1H), 7.73 (d, J=8.7 Hz, 1H), 7.69 (dd, J=8.7 and 1.9 Hz, 1H), 7.39 (dd, J=8.0 and 4.7 Hz, 1H); LRMS (m/z, relative intensity) 263 (19), 262 (M$^+$, 100), 234 (57), 233 (37), 206 (17). Analytical calculated for C$_{15}$H$_{10}$N$_4$O.0.25 H$_2$O: C, 67.54; H, 3.97; N, 21.00. Found: C, 67.82; H, 3.99; N, 20.68.

EXAMPLE 5

1-(3-(Cyclohexen-1-yl)indol-5-yl)-5-methylbenzimidazole

To a stirred solution of sodium (0.325 g, 14.2 mmol, 7.0 equivalents) in absolute methanol (10 mL) was added 1-(indol-5-yl)-5-methylbenzimidazole (0.500 g, 2.02 mmol) and cyclohexanone (0.84 mL, 8.08 mmol, 4.0 equivalents), and the resulting reaction solution was heated at reflux under nitrogen for 12 hours. The resulting mixture was evaporated under reduced pressure, and the residue was column chromatographed using silica gel (approximately 25 g) and eluted with 20% ethyl acetate in methylene chloride to afford the title compound (0.160 g, 0.49 mmol, 24%) as a pale yellow foam. Mp, 101.0°–102.0° C.; $R_f$=0.75 in 5% MeOH in methylene chloride; $^1$H NMR (CD$_3$OD) d 8.25 (s, 1H), 7.88 (s, 1H), 7.53–7.50 (m, 2H), 7.35–7.33 (m, 2H), 7.21 (br d, J=8.5 Hz, 1H), 7.12 (d, J=8.2 Hz, 1Hz), 6.14 (br m, 1H), 4.90 (s, 1 exchangeable H), 2.46 (s, 3H), 2.19 (br m, 2H), 1.86–1.75 (m, 2H), 1.75–1.63 (m, 2H); IR (KBr) 2929, 2859, 1615, 1579, 1494, 1447 cm$^{-1}$.

EXAMPLE 6

1-(3-Cyclohexylindol-5-yl)-5-methylbenzimidazole

A mixture of 1-(3-(cyclohexen-1-yl)indol-5-yl)-5-methylbenzimidazole (0.110 g, 0.34 mmol), 10% Pd on carbon (0.027 g), and absolute ethanol (2 mL) was shaken under an atmosphere of hydrogen (3 atm) for 72 hours. The resulting reaction mixture was filtered through Celite®, and the filtrate was evaporated under reduced pressure to afford the title compound (0.090 g, 80%) as a dark brown foam. Mp, decomposes 120° C.; $^1$H NMR (DMSO-d$_6$) d 11.5 (br s, NH), 8.41 (s, 1H), 7.73 (s, 1H), 7.56–7.52 (m, 2H), 7.39 (d, J=8.4 Hz, 1H), 7.27–7.24 (m, 2H), 7.13 (d, J=8.0 Hz, 1H), 2.88–2.75 (m, 1H), 2.45 (s, 3H), 2.10–1.60 (m, 10 H); IR (KBr) 2924, 2851, 1612, 1580, 1492, 1447 cm$^{-1}$; FAB LRMS (m/z, relative intensity) 331 (25), 330 ([MH]$^+$, 100). HRMS calculated for C$_{22}$H$_{23}$N$_3$: 329.1887. Found: 329.1874.

EXAMPLE 7

1-(3-Benzoylindol-5-yl)-5-methylbenzimidazole

To a stirred solution of 1-(indol-5-yl)-5-methylbenzimidazole (1.00 g, 4.04 mmol, 2.0 equivalents) in anhydrous benzene (10 mL) at 0° C. under nitrogen was added a solution of ethyl magnesium bromide in ether (3.0M, 1.33 mL, 4.00 mmol, 2.0 equivalents) dropwise, and the resulting reaction solution was stirred at 0° C. under nitrogen for 30 minutes. Then, benzoyl chloride (0.23 mL, 1.98 mmol) was added dropwise rapidly to the reaction solution, and the resulting mixture was stirred at room temperature under nitrogen for 30 min. A saturated solution of sodium hydrogen carbonate (25 mL) was then added to the reaction mixture, and the resulting aqueous mixture was extracted with ethyl acetate (2×25 mL). The extracts were combined, dried (MgSO$_4$), and evaporated under reduced pressure. The residue (2.1 g) was column chromatographed using silica gel (approximately 100 g) and eluted with ethyl acetate/hexanes (1:1) to afford the title compound (0.045 g, 0.13 mmol, 6%) as a white foam. $R_f$=0.65 in ethyl acetate/hexanes (1:1); $^1$H NMR (CD$_3$OD) d 8.05–7.95 (m, 3H), 7.81 (d, J=6.8 Hz, 1H), 7.71 (d, J=8.5 Hz, 1H), 7.61–7.39 (m, 7H), 7.18 (d, J=8.4 Hz, 1H), 2.48 (s, 3H); FAB LRMS (m/z, relative intensity) 352 ([MH]$^+$, 78%), 248 ([MH]$^+$ —Ph (CO), 100).

EXAMPLE 8

General Synthesis of 5-(2-Nitroarylamino)-1H-indoles

A solution of the 5-amino-1H-indole (2.00 mmol), a 2-nitrohaloarene (3.00 mmol, 1.5 eq), and a base (3.00 mmol) in an appropriate inert solvent (10 mL) was heated at reflux under nitrogen for 1 to 24 hours, depending on the substrate. The solvents were evaporated under reduced pressure, and the residue was column chromatographed using silica gel (approximately 50 g) and eluted with an appropriate solvent system to afford the 5-(2-nitroarylamino)-1H-indole derivative. In some cases recrystallization of the solid obtained from chromatography was performed to obtain analytically pure samples of the appropriate 5-(2-nitroarylamino)-1H-indole.

Following this procedure the following compounds were prepared.

A. 5-(4-Cyano-2-nitrophenylamino)-1H-indole

5-Aminoindole (0.264 g, 2.00 mmoles) and 4-chloro-3-nitrobenzonitrile (0.444 g, 3.00 mmoles) were combined with triethylamine (0.42 ml, 3.01 mmoles) in absolute ethanol and the reaction was heated at reflux under nitrogen for 3 hours. After evaporation of the solvent, the residue was chromatographed using ether/hexanes [1:1] to afford the title compound (79%) as a red amorphous solid. Mp, decomposes 134° C.; $^{13}$C NMR (DMSO-$d_6$) $\delta$146.9, 137.3, 134.8, 131.9, 131.3, 128.9, 128.3, 126.9, 119.8, 118.2, 117.9, 117.2, 112.5, 101.5, 97.4; LRMS (m/z, relative intensity) 278 (M$^+$, 100), 261 (31), 244 (73), 231 (78). HRMS calculated for $C_{15}H_{10}N_4O_2$: 278.0802. Found: 278.0808. Analytical calculated for $C_{15}H_{10}N_4O_2$: C, 64.74; H, 3.62; N, 20.13. Found: 64.84; H, 3.57; N, 20.13.

B. 5-(4-Methyl-2-nitrophenylamino)-1H-indole

5-Aminoindole (0.264 g, 2.00 mmoles) and 4-fluoro-3-nitrotoluene (0.465 g, 3.00 mmoles) were combined with triethylamine (0.42 ml, 3.01 mmoles) in which 4-fluoro-3-nitrotoluene was the only solvent and the reaction was heated at 225° C. under nitrogen for 18 hours. Chromatography using ether/hexanes [1:1 ] afforded the title compound (90%) as a red amorphous solid. Mp, decomposes 94° C.; $R_f$=0.55 in ethyl acetate/hexanes [1:1]; $^{13}$C NMR (CDCl$_3$) $\delta$143.4, 137.3, 134.2, 131.8, 131.1, 128.7, 126.1, 125.6, 120.8, 117.9, 116.2, 112.1, 102.8, 20.1; LRMS (m/z, relative intensity) 267 (M$^+$, 45), 250 (5), 233 (20), 220 (13). HRMS calculated for $C_{15}H_{13}N_3O_2$: 267.1005. Found: 267.0993.

C. 5-(3-Nitropyrid-2-ylamino)-1H-indole

5-Aminoindole (0.264 g, 2.00 mmoles) and 2-chloro-3-nitropyridine (0.476 g, 3.00 mmoles) were combined with triethylamine (0.42 ml, 3.01 mmoles) in absolute ethanol. The reaction was heated at room temperature under nitrogen for 72 hours. The resulting reaction mixture was filtered to afford the title compound (69%) as a dark red solid. Mp, 162.0°-163.5° C.; $R_f$=0.6 in diethyl ether; $^{13}$C NMR (DMSO-$d_6$) $\delta$155.6, 150.5, 135.5, 133.5, 129.7, 127.9, 127.6, 125.9, 118.5, 115.0, 113.4, 111.2, 101.2. Analytical calculated for $C_{13}H_{10}N_4O_2$: C, 61.41; H, 3.96; N, 22.04. Found: 61.22; H, 3.80; N, 22.08.

I claim:

1. A compound of the formula

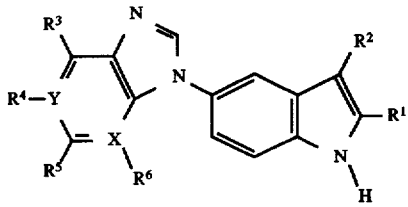

wherein X and Y are independently carbon or nitrogen;

R$^1$ and R$^2$ are independently selected from hydrogen, ($C_1$–$C_6$)alkyl, aryl, —($C_1$–$C_3$)alkylaryl, —(CH$_2$)$_n$—($C_4$–$C_7$)cycloalkyl, cyclohexen-1-yl, benzoyl, —(CH$_2$)$_n$CHO, —(CH$_2$)$_n$CO$_2$R$^7$, —(CH$_2$)$_n$CONR$^7$R$^8$, 3-succinamido, unsaturated heterocycle, benzo-fused heterocycle, —($C_1$–$C_3$)alkyl-unsaturated heterocycle, and —($C_1$–$C_3$)alkyl-benzo-fused heterocycle; wherein said unsaturated heterocycle and unsaturated heterocycle moiety of said —($C_1$–$C_3$)alkyl-unsaturated heterocycle are selected, independently, from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, 1,2,5-thiadiazinyl, 1,2,5-oxathiazinyl, and 1,2,6-oxathiazinyl; wherein said benzo-fused heterocycle and the benzo-fused heterocyclic moiety of said —(CFC$_3$)alkyl-benzo-fused heterocycle are selected, independently, from benzoxazolyl, benzothiazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl and benzoxazinyl; wherein each of said unsaturated heterocycle, benzo-fused heterocycle, —($C_1$–$C_3$)alkyl-unsaturated heterocycle and —($C_1$–$C_3$)alkyl-benzo-fused heterocycle may optionally be substituted on one or more ring carbon atoms with from zero to three substituents, said substituents being independently selected from bromo, chloro, fluoro, ($C_1$–$C_5$)alkyl, ($C_1$–$C_5$)alkoxy, ($C_1$–$C_5$) alkylthio, ($C_1$–$C_5$)alkylamino, ($C_1$–$C_4$)alkylsulfonyl, ($C_1$–$C_5$)dialkylamino, hydroxy, amino, nitro, cyano, trifluoromethyl,

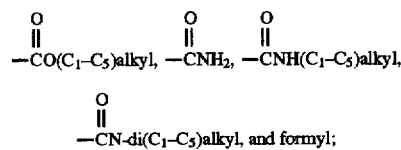

wherein said aryl groups and the aryl moieties of said ($C_1$–$C_3$)alkylaryl groups are independently selected from phenyl and substituted phenyl, wherein said substituted phenyl may be substituted with from one to three substituents independently selected from ($C_1$–$C_4$)alkyl, halogen, hydroxy, cyano, carboxamido, nitro, and ($C_1$–$C_4$)alkoxy;

R$^3$, R$^4$, R$^5$, and R$^6$ are independently selected from hydrogen, ($C_1$–$C_6$)alkyl, aryl, —($C_1$–$C_3$)alkylaryl, —CN, —CHO, CO$_2$R$^9$, —NO$_2$, —CONR$^9$R$^{10}$, —(CH$_2$)$_p$OH, —(CH$_2$)$_p$OR$^9$, —(CH$_2$)$_p$NR$^9$R$^{10}$ and halogen; wherein said aryl groups and the aryl moieties of said —($C_1$–$C_3$)alkylaryl groups are independently selected from phenyl and substituted phenyl, wherein said substituted phenyl may be substituted with from one to three substituents independently selected from ($C_1$–$C_4$)alkyl, halogen, hydroxy, cyano, carboxamido, nitro, and ($C_1$–$C_4$)alkoxy;

R$^7$, R$^8$, R$^9$, and R$^{10}$ are independently selected from hydrogen, ($C_1$–$C_6$)alkyl, aryl, —($C_1$–$C_3$)alkylaryl, unsaturated heterocycle, benzo-fused heterocycle, —($C_1$–$C_3$)alkyl-unsaturated heterocycle, and —($C_1$–$C_3$)alkyl-benzo-fused heterocycle; wherein said unsaturated heterocycle and unsaturated heterocycle moiety of said —($C_1$–$C_3$)alkyl-unsaturated heterocycle are selected independently from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, 1,2,5-thiadiazinyl, 1,2,5-oxathiazinyl, and 1,2,6-oxathiazinyl; wherein said benzo-fused heterocycle and the benzo-fused heterocyclic moiety of said —($C_1$–$C_3$)alkyl-benzo-fused heterocycle are selected independently from benzoxazolyl, benzothiazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl and benzoxazinyl; wherein each of said unsaturated heterocycle, benzo-fused heterocycle, —(C₁-C₃)alkyl-unsaturated heterocycle and —(C₁-C₃)alkyl-benzo-fused heterocycle may optionally be substituted on one or more ring carbon atoms with from zero to three substituents, said substituents being independently selected from bromo, chloro, fluoro, (C₁-C₅)alkyl, (C₁-C₅)alkoxy, (C₁-C₅)alkylthio, (C₁-C₅)alkylamino, (C₁-C₄)alkylsulfonyl, (C₁-C₅)dialkylamino, hydroxy, amino, nitro, cyano, trifluoromethyl,

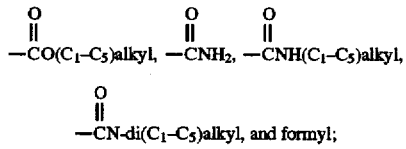

wherein said aryl groups and the aryl moieties of said —(C₁-C₃)alkylaryl groups are independently selected from phenyl and substituted phenyl, wherein said substituted phenyl may be substituted with from one to three substituents independently selected from (C₁-C₄)alkyl, halogen, hydroxy, cyano, carboxamido, nitro, and (C₁-C₄)alkoxy;

n is 0, 1, 2, or 3; and p is 0, 1, or 2;

or a pharmaceutically acceptable salt thereof.

2. A compound according to claim 1, wherein X is carbon; Y is carbon and R₁ is hydrogen.

3. A compound according to claim 1, said compound being selected from:
5-cyano-1-(indol-5-yl)benzimidazole;
5-cyano-1-(3-formylindol-5-yl)benzimidazole;
1-(indol-5-yl)-5-methylbenzimidazole;
5-cyano-1-(3-(cyclohexen-1-yl)indol-5-yl)benzimidazole;
1-(3-formylindol-5-yl)-3H-pyrido[4,5-b]imidazole;
1-(3-(cyclohexen-1-yl)indol-5-yl)-5-methylbenzimidazole;
1-(3-cyclohexylindol-5-yl)-5-methylbenzimidazole; and
1-(3-benzoylindol-5-yl)-5-methylbenzimidazole;
or a pharmaceutically acceptable salt thereof.

4. A pharmaceutical composition for treating a condition or disorder selected from anxiety, panic attacks, sleep disorders, seizures, memory loss, convulsions, and drug abuse in a mammal, comprising an amount of a compound according to claim 1, or a pharmaceutically accepted salt thereof, effective in treating such condition or disorder and a pharmaceutically acceptable carrier.

5. A pharmaceutical composition for treating a condition or disorder arising from an increase or decrease in benzodiazepine receptor neurotransmission in a mammal, comprising an amount of a compound according to claim 1, or a pharmaceutically accepted salt thereof, effective in treating such a condition or disorder and a pharmaceutically acceptable carrier.

6. A pharmaceutical composition for antagonizing or agonizing the benzodiazepine receptor in a mammal, comprising a benzodiazepine receptor antagonizing or agonizing effective amount of a compound according to claim 1, or a pharmaceutically accepted salt thereof and a pharmaceutically acceptable carrier.

7. A pharmaceutical composition for treating a disorder or condition selected from anxiety, panic attacks, sleep disorders, seizures, memory loss, convulsions, and drug abuse in a mammal, comprising a benzodiazepine receptor antagonizing or agonizing effective amount of a compound of according to claim 1, or a pharmaceutically accepted salt thereof and a pharmaceutically acceptable carrier.

8. A method for treating or preventing a condition selected from anxiety, panic attacks, sleep disorders, seizures, memory loss, convulsions, and drug abuse in a mammal, comprising administering to said mammal requiring such treatment an amount of a compound according to claim 1, or a pharmaceutically accepted salt thereof, effective in treating or preventing such condition or disorder.

9. A method for treating a condition or disorder arising from an increase or decrease in benzodiazepine receptor neurotransmission in a mammal, comprising administering to said mammal requiring such treatment an amount of a compound according to claim 1, or a pharmaceutically accepted salt thereof, effective in treating such condition or disorder.

10. A method of antagonizing or agonizing the benzodiazepine receptor in a mammal, comprising administering to said mammal a benzodiazepine receptor antagonizing or agonizing amount of a compound according to claim 1, or a pharmaceutically accepted salt thereof.

11. A method for treating a condition or disorder selected from anxiety, panic attacks, sleep disorders, seizures, memory loss, convulsions, and drug abuse in a mammal, comprising administering to said mammal a benzodiazepine receptor antagonizing or agonizing amount of a compound according to claim 1, or a pharmaceutically accepted salt thereof.

* * * * *